(12) United States Patent
Benda et al.

(10) Patent No.: US 10,887,948 B2
(45) Date of Patent: Jan. 5, 2021

(54) SAUNA HEATING PANEL POWER DISTRIBUTION SYSTEMS AND METHODS

(71) Applicant: TyloHelo Inc., Cokato, MN (US)

(72) Inventors: Steven J. Benda, Cokato, MN (US); Ragis H. C. Kao, Taipei (TW)

(73) Assignee: TyloHelo Inc., Cokato, MN (US)

(*) Notice: Subject to any disclaimer, the term of this patent is extended or adjusted under 35 U.S.C. 154(b) by 594 days.

(21) Appl. No.: 15/728,145

(22) Filed: Oct. 9, 2017

(65) Prior Publication Data

US 2018/0146513 A1 May 24, 2018

Related U.S. Application Data

(63) Continuation of application No. 13/665,040, filed on Oct. 31, 2012, now Pat. No. 9,788,367.

(Continued)

(51) Int. Cl.
*H05B 3/06* (2006.01)
*A61H 33/06* (2006.01)
(Continued)

(52) U.S. Cl.
CPC ............ *H05B 3/06* (2013.01); *A61H 33/063* (2013.01); *A61H 33/066* (2013.01);
(Continued)

(58) Field of Classification Search
CPC .......... F24D 13/024; A61N 2005/0659; A61H 2201/10; A61H 33/066; A61H 33/063; Y02B 30/26
(Continued)

(56) References Cited

U.S. PATENT DOCUMENTS 5,218,185 A 6/1993 Gross et al.
5,811,767 A 9/1998 Wildi et al.
(Continued)

FOREIGN PATENT DOCUMENTS

| CA | 2794059 | 7/2014 |
|---|---|---|
| EP | 2587169 | 5/2013 |
| WO | 2011097086 | 8/2011 |

OTHER PUBLICATIONS

Response to Communication Pursuant to Article 94(3) EPC for European Patent Application No. 12190904.8 filed with the EPO Jan. 22, 2018 (52 pages).

(Continued)

*Primary Examiner* — Dana Ross
*Assistant Examiner* — Kuangyue Chen
(74) *Attorney, Agent, or Firm* — Pauly, DeVries Smith & Deffner LLC

(57) ABSTRACT

Power feed connections and sauna heating panels include a power feed having a first insulated conductor electrically coupled to a first terminal and a second insulated conductor electrically coupled to a second terminal. The first and second terminals are electrically coupled with at least one heating element. In some cases the power feed includes a supply portion, a connection portion, and an extension portion. The extension portion has one or more conductors in a twisted configuration extending away from the first and second terminals. In some cases the power feed includes an extension conductor portion coupled to a return conductor portion in a twisted configuration. The extension portion extends away from a second terminal past a second connection point and the return portion returns back to and connects to the second connection point at the second terminal. Methods for providing power connections to heating panels are also provided.

22 Claims, 10 Drawing Sheets

Related U.S. Application Data

(60) Provisional application No. 61/628,455, filed on Oct. 31, 2011.

(51) Int. Cl.
*F24D 13/02* (2006.01)
*A61N 5/06* (2006.01)

(52) U.S. Cl.
CPC ...... *F24D 13/024* (2013.01); *A61H 2033/061* (2013.01); *A61H 2201/10* (2013.01); *A61N 2005/0659* (2013.01); *Y02B 30/00* (2013.01)

(58) Field of Classification Search
USPC .......................................................... 219/213
See application file for complete search history.

(56) References Cited

U.S. PATENT DOCUMENTS

| | | |
|---|---|---|
| 6,734,404 B2 | 5/2004 | Hays et al. |
| 8,692,168 B2 | 4/2014 | Benda et al. |
| 9,788,367 B2 | 10/2017 | Benda et al. |
| 2003/0156831 A1 | 8/2003 | Schaeffer et al. |
| 2003/0178415 A1 | 9/2003 | Hays et al. |
| 2005/0139370 A1 | 6/2005 | Whidden et al. |
| 2005/0247700 A1 | 11/2005 | Kochman et al. |
| 2007/0182498 A1 | 8/2007 | Zumoto et al. |
| 2011/0315672 A1 | 12/2011 | Benda et al. |
| 2013/0105458 A1 | 5/2013 | Benda et al. |

OTHER PUBLICATIONS

"Communication Pursuant to Article 94(3) EPC," for European Patent Application No. 12190904.8 dated Sep. 28, 2017 (4 pages).
"Extended European Search Report," for European Patent Application No. 12190904.8 dated Oct. 22, 2015 (7 pages).
"File History," for U.S. Appl. No. 13/665,040.
"Office Action," for Canadian Patent Application No. 2,784,059 dated Nov. 4, 2013 (2 pages).
Response to Extended European Search Report for European Patent Application No. 12190904.8 filed with the EPO May 25, 2016 (58 pages).
"Response to Office Action," for Canadian Patent Application No. 2,784,059 filed with CIPO Feb. 3, 2014 (10 pages).

SAUNA HEATING PANEL POWER DISTRIBUTION SYSTEMS AND METHODS

RELATED APPLICATIONS

This application is a continuation application of prior U.S. application Ser. No. 13/665,040, filed Oct. 31, 2012, which claims the benefit of U.S. Provisional Application No. 61/628,455, filed Oct. 31, 2011, the contents each of which are hereby incorporated by reference in their respective entireties.

FIELD

This disclosure relates generally to saunas with electric heating panels, including infrared heating panels, and relates more particularly to power distribution systems and methods for supplying power to sauna heating panels.

BACKGROUND

Sauna systems throughout history have employed various methods of heating a space to provide the therapeutic and cleansing effects of heat. As is well known, heat causes the human body to perspire and can also provide soothing and therapeutic effects to muscles and joints. Methods of heating a sauna include using open fires, enclosed stoves, and steam generators among others. While some forms of heat generation are effective to varying degrees, they can also present drawbacks. For example, the open fires found in old forms of Scandinavian saunas provided direct open flame heating, but also created intensely smoky rooms with short lived heat. Wood stoves enable a more controlled heat over a greater period of time, but also shield the heat due to the enclosed nature of the stove.

Saunas using electrically energized heaters have been developed. These include electrically-resistive heaters and energized radiant heaters. Some types of radiant heat systems employ infrared heating panels to generate electromagnetic radiation within the infrared spectrum. When absorbed by the body of a sauna user, the infrared radiation excites the molecules within the body to generate warming. Whereas steam or warm air generally only heat the skin and tissue directly beneath by conduction, infrared radiation extends deeply penetrates the body (e.g., to about 1.5 inches) to more effectively and comfortably warm the body to a sweating temperature without the use of a conductive medium.

As is known, an electromagnetic field (also EMF or EM field) such as an EM field within the infrared spectrum can be caused by electric charges passing through a conductor as a current. Electromagnetic fields can generally be considered as including electric fields and magnetic fields interacting together. Electric fields are caused by electric charges and electric field intensity is typically measured in Volts/meter. Magnetic fields are caused by an electric current of moving charges, and magnetic field or flux density is typically measured in gauss. The term electromagnetic radiation (also EMR) is sometimes used to refer to EM fields radiating through space apart from their source.

Radiant heating systems are generally powered by conventional alternating current (AC) power sources, such as 110 volt, 60 Hz AC in the United States or 230 volt, 50 Hz AC in Europe. Such heating systems thus tend to generate some amount of low frequency (e.g., 50-60 Hz) electromagnetic radiation in addition to the desired infrared radiation utilized for heating. It has been estimated that in some cases infrared sauna systems may generate low frequency EM radiation with magnetic field levels as high as 60 milligauss. In comparison, areas under high voltage transmission lines have been measured with low frequency magnetic field levels as high as 1.9 milligauss and outdoor areas in open spaces have been measured with low frequency magnetic field levels as low as 0.3 milligauss.

Concerns about high levels of low frequency radiation have led to multiple methods for reducing the level of low frequency EM radiation in heating systems and saunas, including infrared heating systems used in saunas. These include increasing the distance from the emitting source, reducing the exposure time to the radiation level and/or increasing shielding between the human body and the emitting source. In addition, attempts have also been made to reduce the level of low frequency EM radiation through EM cancellation schemes, such as by producing multiple low frequency EM fields that tend to cancel one another.

SUMMARY

Some embodiments that will be described herein generally provide power feeds, power feed connections, heating panels, saunas, and/or methods relating to design configurations that can in some cases reduce the electromagnetic field emissions emanating from the power connection to an electric heating panel.

According to one aspect, an electrically-powered heating panel is provided. The heating panel includes a substrate and at least one heating element positioned on the substrate. The heating panel also includes a first terminal electrically coupled to the at least one heating element and a second terminal electrically coupled to the at least one heating element. The second terminal is in some cases positioned adjacent to the first terminal on the substrate. The heating panel further includes a power feed that can be described as including a supply portion, a connection portion, and an extension portion. The supply portion includes a first insulated conductor and a second insulated conductor, with the conductors having a twisted configuration about each other. The connection portion includes a first electrical coupling between the first insulated conductor and the first terminal and also includes a second electrical coupling between the second insulated conductor and the second terminal. The extension portion includes one or more insulated conductors also in a twisted configuration. The extension portion conductors extend over the substrate away from the first and the second terminals such that current flows in opposite directions through the extension portion in order to reduce electromagnetic field emissions generated by the power feed.

According to another aspect, a heating panel for an infrared sauna is provided. The heating panel, also referred to as an infrared heating panel, includes a substrate and at least one infrared heating element positioned on the substrate. The infrared heating element is configured to provide heat for a user of the infrared sauna. A first terminal of the heating panel is electrically coupled to the at least one infrared heating element, as is a second terminal. The heating panel includes first and second insulated conductors for providing power to the at least one infrared heating element. The first insulated conductor is electrically connected to the first terminal at a first connection point. The second insulated conductor is twisted about the first insulated conductor and electrically connected to an extension conductor portion. The extension conductor portion includes an insulated conductor extending past the second terminal. The heating panel further includes a return conductor portion that is electrically coupled to the extension conductor portion. The return conductor portion includes an insulated conductor returning back to and being electrically connected to the second terminal at a second connection point. In addition, the return conductor portion is twisted about the extension conductor portion.

According to another aspect, a method for providing a power connection to a heating panel of a sauna is provided. The method includes providing a heating panel and a power feed. The heating panel includes a substrate, at least one heating element, and first and second terminals electrically coupled to the at least one heating element. The power feed includes a first insulated conductor, a second insulated conductor in a twisted configuration with the first insulated conductor, an extension conductor portion electrically connected to the second insulated conductor, and a return conductor portion electrically coupled to the extension conductor portion. The return conductor portion is twisted about the extension conductor portion. The method further includes electrically connecting the first insulated conductor to the first terminal and extending the extension conductor portion across the substrate past the second terminal. The method also includes returning the return conductor portion across the substrate to the second terminal and electrically connecting the return conductor portion to the second terminal.

Some embodiments may optionally provide none, some, or all of the following advantages, though other advantages not listed here may also be provided. In some cases, one or both of an extension conductor portion and/or return conductor portion of a power feed may be an integral portion of one of the insulated conductors providing power to the heating panel. In some cases, the return conductor is instead a separate insulated conductor physically connected to the end of the extension conductor. In some cases, the return conductor portion can be made by cutting off a portion of one of the insulated conductors of the power feed, twisting the portion about the extension conductor portion, electrically connecting the portion to the end of the extension conductor portion, and electrically connecting the opposite end of the portion to the second terminal.

According to some embodiments, an extension portion of a power feed can include a thermal switch or a thermal breaker such as a thermal circuit breaker, whose leads may in some cases form all or part of one or more of extension conductor and return conductor portions of the extension portion. In some cases, such an extension portion and thermal switch can extend over the substrate between the terminals and the at least one heating element, and the thermal switch can be positioned on or affixed to the at least one heating element.

According to some embodiments, a heating panel may include a containment system that contains one or more portions of the power feed and/or connections to the heating panel and secures them to a substrate of the heating panel. In some cases the containment system includes a shell made from a nonconductive material such as a polymer. The containment system may also include a nonconductive filling within the shell to adhere the shell and power feed to the heating panel substrate. For example, in some cases, the nonconductive filling may include an insulating adhesive.

According to some embodiments, a power feed bringing power to a heating panel can include first and second insulated conductors and an uninsulated ground conductor in a twisted configuration. In some cases a metallic shielding surrounds the first and second insulated conductors and the uninsulated ground conductor. An insulating jacket can also surround the metallic shielding assembly.

These and various other features and advantages will be apparent from a reading of the following description of the drawings and detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
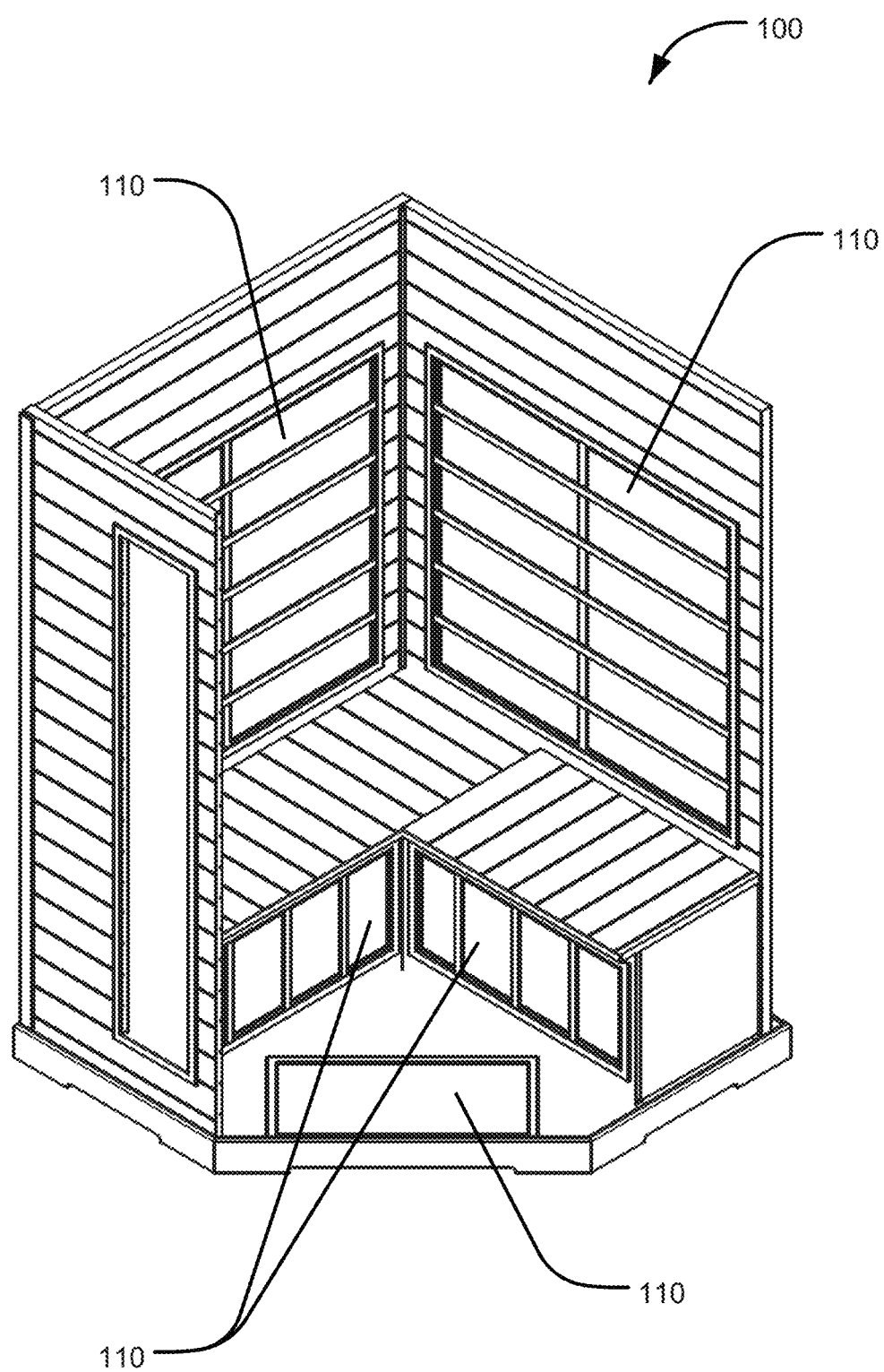
FIG. 1 is a perspective view of a sauna according to some embodiments.

FIG. 1 is a perspective view of a sauna 100 according to an embodiment of the invention. The sauna 100 includes a number of heaters 110, each having one or more heating elements (not shown). In this example, the heaters 110 are illustrated as infrared heating panels 110. When powered, the infrared heating panels 110 generate infrared radiation for warming a person within the sauna 100. It should be appreciated that the sauna 100 depicted in FIG. 1 is just one example of many possible designs. It is contemplated that some embodiments may include a wide variety of sauna designs. In addition, the infrared heating panels 110 as well as other types of heating panels or electrical heaters may be provided with a number of physical dimensions and configurations to accommodate the overall sauna design and provide a desired heating environment. Embodiments are not limited in this regard. As just one type of example, the sauna 100 shown in FIG. 1 includes a number of differently sized heating panels 110 positioned on the walls, floor, and bench of the sauna 100.

As will be discussed further herein, in some embodiments the heating panels or heaters 110 have a power connection portion that is configured to reduce the magnitude of certain EM fields generated by the power feed (also referred to in some cases as a power harness) connection to the heating panels 110. For example, in some cases two or more parts of the power feed connection portion may generate multiple EM fields that counteract and/or cancel each other and thus tend to reduce the overall level of certain EM fields in the vicinity of the connection portion. Reduced or cancelled EM fields can in some cases allow the heating panels 110 to be positioned in closer proximity to sauna users, thus increasing the effectiveness of the heating panels 110 while also reducing exposure to certain EM fields.

Figure 2:
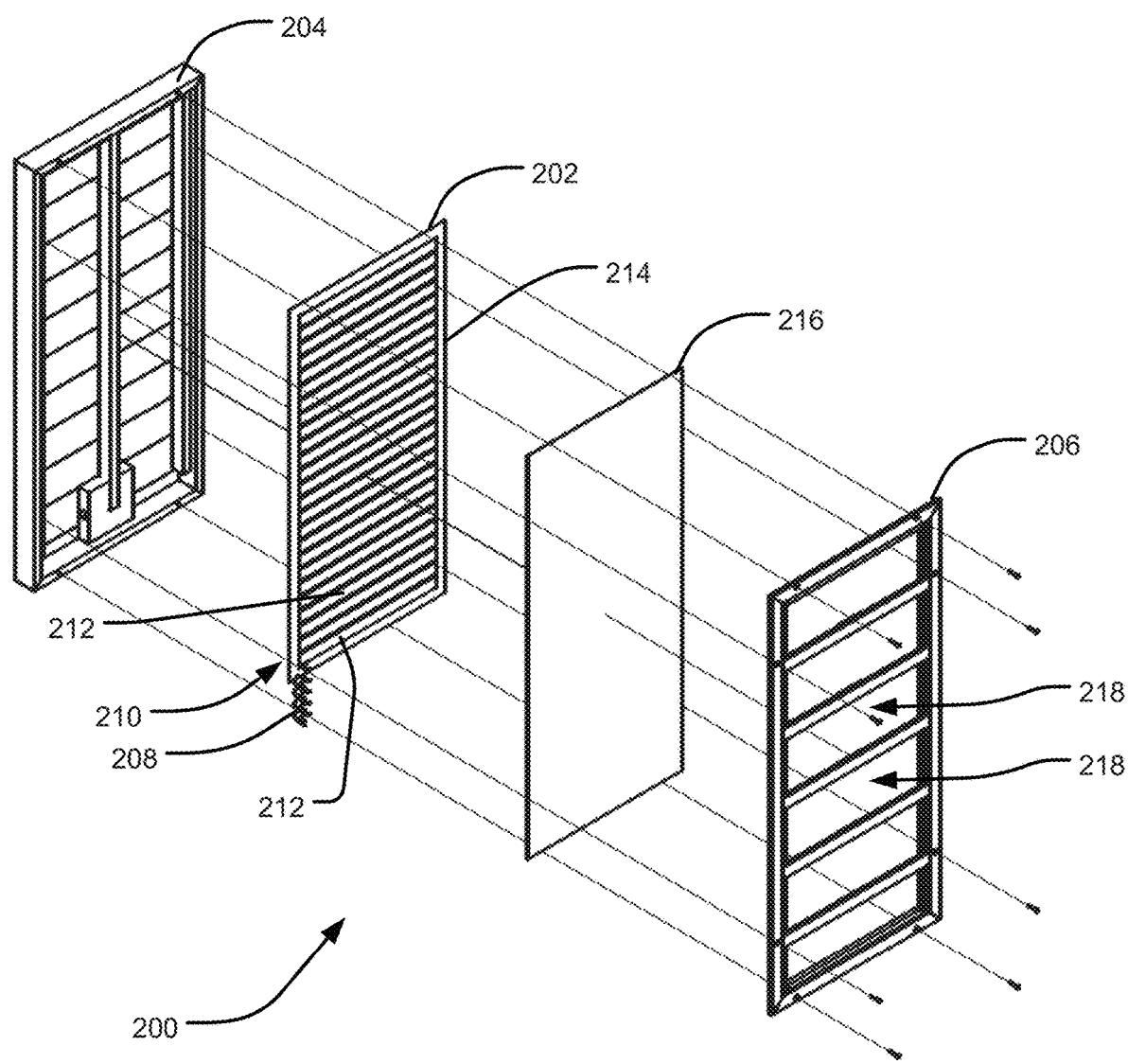
FIG. 2 is an exploded assembly view of an infrared heating panel assembly according to an embodiment.

FIG. 2 is an exploded assembly view of an infrared heating panel assembly 200 according to some embodiments. The panel assembly 200 generally provides an enclosure for a heating panel 202, which is an example of one of the infrared heating panels 110 shown in conjunction with the sauna 100 in FIG. 1. In certain embodiments the panel assembly 200 includes a back frame member 204 and a front frame member 206 that enclose the heating panel 202 and are coupled with fastening members such as screws. The panel assembly 200 includes a power feed 208 electrically connected to a power connection portion 210 of the infrared heating panel 202, for electrically connecting the panel 202 to a power source such as a source of alternating current. In general, the infrared heating panel 202 includes multiple infrared heating elements 212 that are positioned on a substrate 214 and electrically coupled to the power connection portion of the panel 202 in order to receive electricity from the power feed connection 208.

Some examples of infrared heating panels and infrared heating elements are described in detail in U.S. patent application Ser. No. 12/966,221, filed Dec. 13, 2010, and titled "Infrared Heating Panels, Systems and Methods," the entire content of which is hereby incorporated by reference. Of course, embodiments described herein and otherwise within the scope of this disclosure are not limited to any particular form or type of heating panel. Accordingly, it should be understood that embodiments employing the principles described herein may provide a power feed connection for one of many different types of electric heaters for a sauna, including infrared heating panels and non-infrared resistive heating panels, and/or generally provide power for electric heating panels apart from saunas.

Returning to FIG. 2, the panel assembly 200 also includes a thermal shielding layer 216 that can be useful for shielding a sauna user from incidental or temporary contact with the heating elements. For example, the thermal shielding layer 216 may be a cloth panel that provides a mild thermal conductivity barrier to act as a thermal shield to minimize discomfort to human skin in the event of direct contact. In some cases the front frame member 206 includes one or more apertures or windows 218 to facilitate radiation/heat flow and the thermal shielding layer 216 is positioned between the panel 202 and the apertures 218.

According to some embodiments, the thermal shielding layer 216 also acts as a ground plane to shield a sauna user from electric fields generated by the heating panel. In some cases the thermal shielding layer 216 is formed from a conductive fabric and then connected by wire to ground potential through, e.g., the power feed connection 208, a panel frame member 204, 206, a conduit, or another suitable surface or component at ground potential.

Of course, other configurations of the thermal panel assembly 200 are also possible and embodiments are not limited to any particular configuration. As just one example, a portion of the assembly 200 shown in FIG. 2 such as the back frame member 204 may be an integral part of a sauna wall.

Figure 3A:
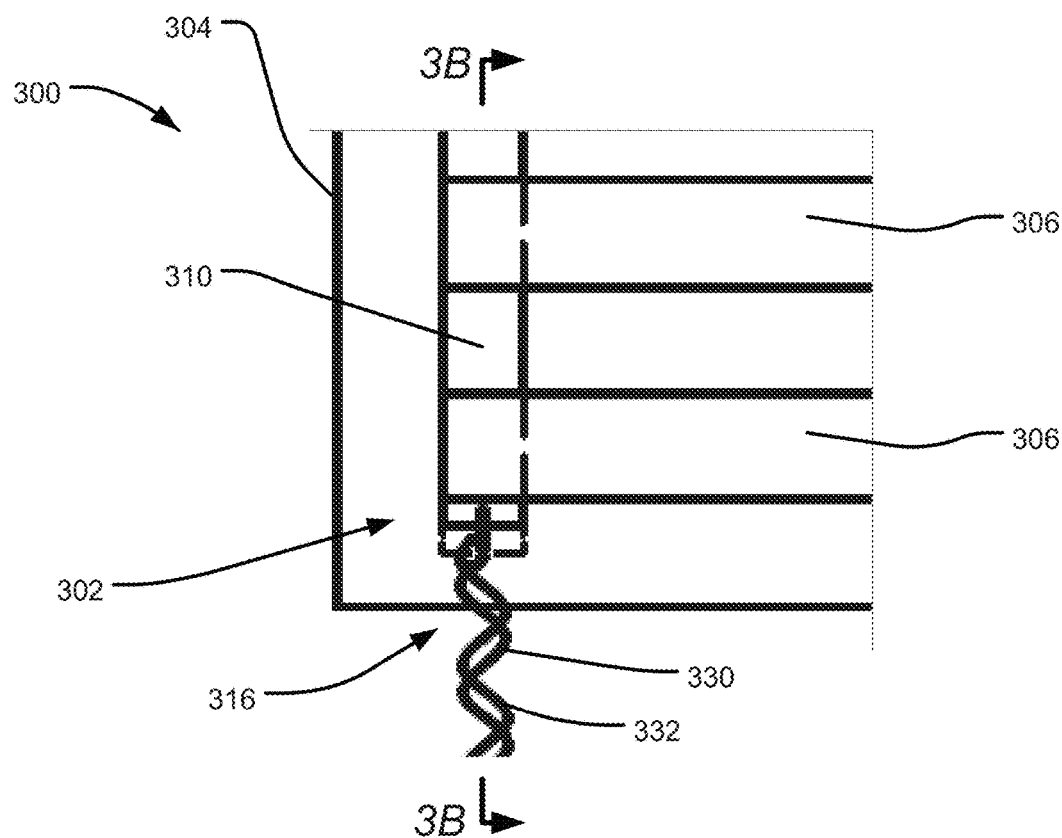
FIG. 3A is a partial side surface view of an infrared heating panel illustrating a power connection portion of the infrared heating panel according to an embodiment.
Figure 3B:
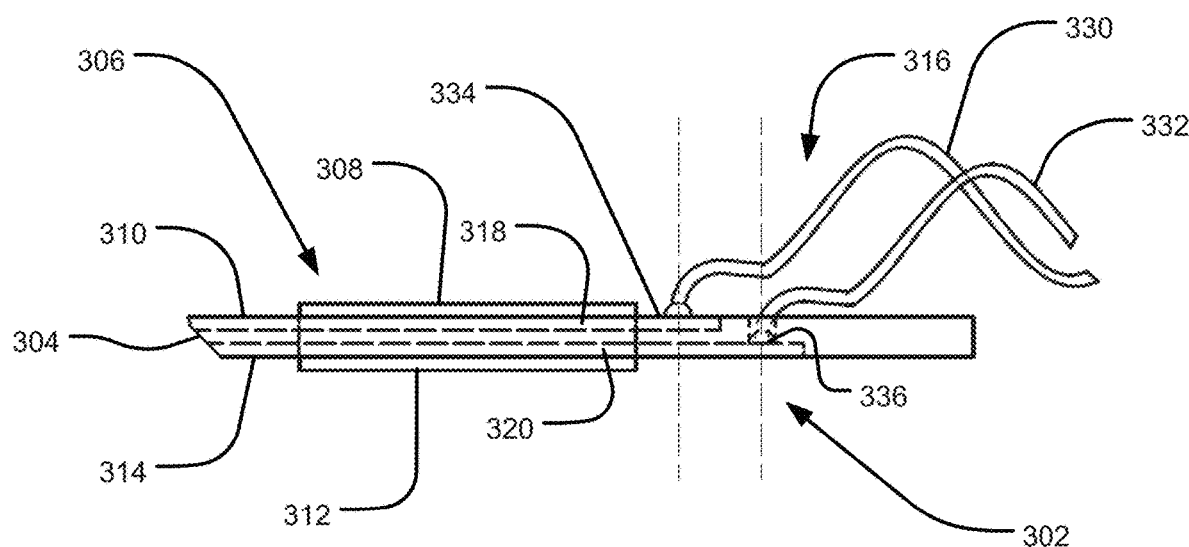
FIG. 3B is an enlarged side end view of the power connection portion of the infrared heating panel of FIG. 3A.

FIG. 3A is a side surface view of part of an infrared heating panel 300 and FIG. 3B is an enlarged side end view of the infrared heating panel 300, both illustrating a power connection portion 302 of the infrared heating panel according to an embodiment. In general, the heating panel 300 generates infrared radiation from electrical power, and is useful for generating heat such as in the infrared sauna 100 shown in FIG. 1. As will be appreciated, the infrared heating panel 300 is similar in some respects to the example of the infrared heating panel 202 illustrated in FIG. 2. While a brief description of certain relevant elements of the heating panel 300 is included herein for convenience, it should be understood that for convenience, this disclosure only provides a high-level and brief summary of some aspects of this example of a heating panel. Other electric heaters are well known in the art and electric heating panels, including infrared heating panels are known. In addition, further details about some examples of infrared heating panels and infrared heating elements are described in U.S. patent application Ser. No. 12/966,221.

Continuing with reference to FIGS. 3A and 3B, it can be seen that the portion of the heating panel 300 includes a substrate 304 that carries multiple heating elements 306 positioned in a row across the panel. Each heating element 306 includes a first segment 308 attached to a first surface 310 of the substrate and a second segment 312 attached to a second surface 314 of the substrate 304. The first and second segments 308, 312 are electrically connected together in series at one end of the segments (not shown), in this embodiment about an unseen edge of the substrate 304. The segments are electrically coupled to a power harness or power feed 316 via a first power bus 318 and a second power bus 320. Although not shown in these figures, it can be appreciated that the power buses 318, 320 can extend across the opposite surfaces 310, 314 of the substrate 304 along one edge in a parallel configuration, connected to each of the heating elements 306.

FIGS. 3A and 3B illustrate one example of a power feed 316 that includes a first insulated conductor 330 and a second insulated conductor 332 electrically coupled to the heating panel 300. In this embodiment the first and second insulated conductors 330, 332 are in a twisted configuration, which in some cases can reduce or eliminate certain low-frequency electromagnetic radiation emanating from the power feed 316 as a result of current flowing through the power feed into the heating panel 300. Although not shown, it will be appreciated that the power feed 316 is suitably configured at its end opposite the heating panel 300 to connect to a source of electrical power, which may be provided at, e.g., a custom junction box or at a more standard utility outlet. In some cases, multiple heating panels may have their respective power feeds routed through the interior spaces of a sauna to a local junction box within one of the walls of the sauna, for powering the group of the heating panels.

The insulated conductors 330, 332 of the power feed electrically connect to the heating panel in the power connection portion 302 of the heating panel. Throughout this disclosure, the electrically conductive points on the heating panel that are physically and electrically connected to the insulated conductors 330, 332 of the power feed (e.g., by solder, a post, a screw, etc.) are generally referred to as electrical terminals. Terminals generally provide a point of electrical contact for connecting the power feed and are also electrically coupled by one or more wires, tracings, busses, or other conductive paths to one or more heating elements on the heating panel. Further, in some cases, a terminal may simply be a conductive portion of a heating element, in which case an insulated conductor could be electrically connected directly to the heating element. Other examples of possible terminal configurations include screws, posts, pads, leads, vias, and/or any other useful conductive part that can be connected to a power feed conductor. In this example shown in FIGS. 3A and 3B, the power connection portion 302 includes an exposed portion 334 of the first power bus 318 and an accessible portion 336 of the second power bus 320, positioned adjacent to the exposed portion 334, to which the first and the second insulated power feed conductors are respectively soldered. Of course, many other terminal configurations are possible and can be used. As just one possible alternative to the configuration shown in FIGS. 3A and 3B, in some cases the second insulated conductor 332 may simply connect to the second power bus 320 from the opposite, second surface 314 of the substrate.

As used herein, the particular location at which a power conductor is specifically connected to a terminal is sometimes referred to as a connection point or an electrical connection point to distinguish from the potentially larger area of a terminal, such as in the case of a pad terminal having an area larger than necessary to connect one of the insulated conductors. In addition, the terms electrically coupled and electrically connected are sometimes used herein to describe different types of conductive paths between components and/or locations, though the terms may be interchanged and should be understood in the context of their usage. For example, in some cases, the term electrically coupled is used to describe an indirect electrical path between two points. For example, an insulated conductor may be described as being electrically coupled to a heating element when the electrical path between the conductor and the heating path extends indirectly between multiple components, such as through a terminal and a bus bar. The term electrically connected is sometimes used to describe a direct, physical and electrical connection between two points, components, and/or parts. For example, an insulated conductor may be described as being electrically connected to a terminal when the conductor is directly soldered to the terminal.

The term low frequency is used generically herein to generally refer to EM radiation emanating from a heating panel at frequencies below the infrared radiation spectrum. Such frequencies may include, for example, very low frequencies (3-30 kHz), ultralow frequencies (300-3 kHz), super low frequencies (30-300 Hz), and/or extremely low frequencies (3-30 Hz), among other higher and lower ranges below infrared frequencies. In some cases, powering a conventional infrared heating panel with an alternating current can generate undesired low frequency or extremely low frequency EM radiation. For example, a 120 VAC, 60 Hz power input may lead to undesirably high levels of EM radiation at about 60 Hz. In some cases examples of the power feed connections described herein (along with other embodiments described herein) can advantageously deliver sufficient power to a sauna heating panel while also reducing low frequency EM radiation levels, e.g., at 60 Hz, to a desirably low level.

Figure 3C:
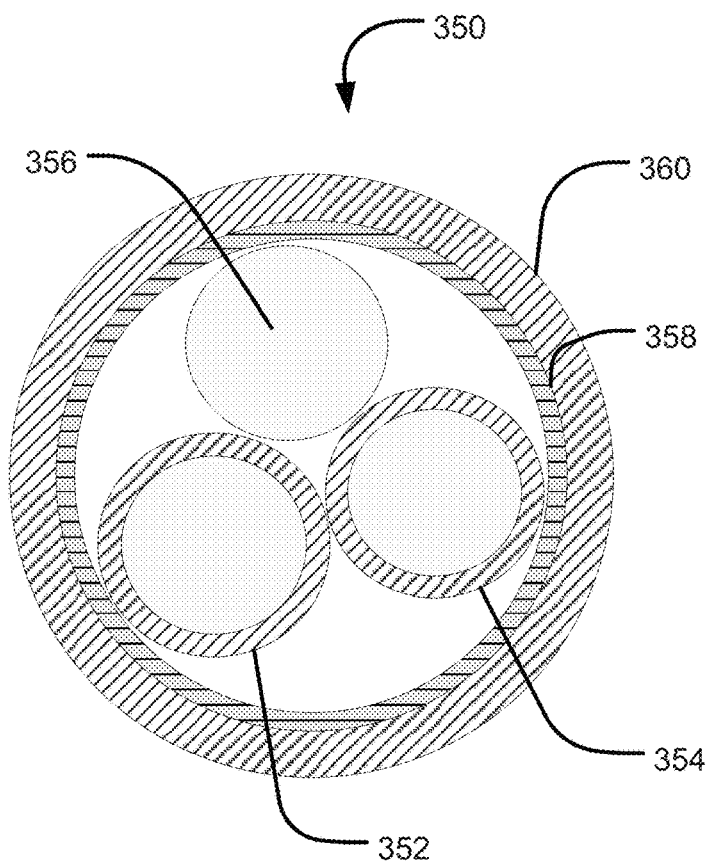
FIG. 3C is a cross-sectional view of a power feed cable according to an embodiment.
Figure 3D:
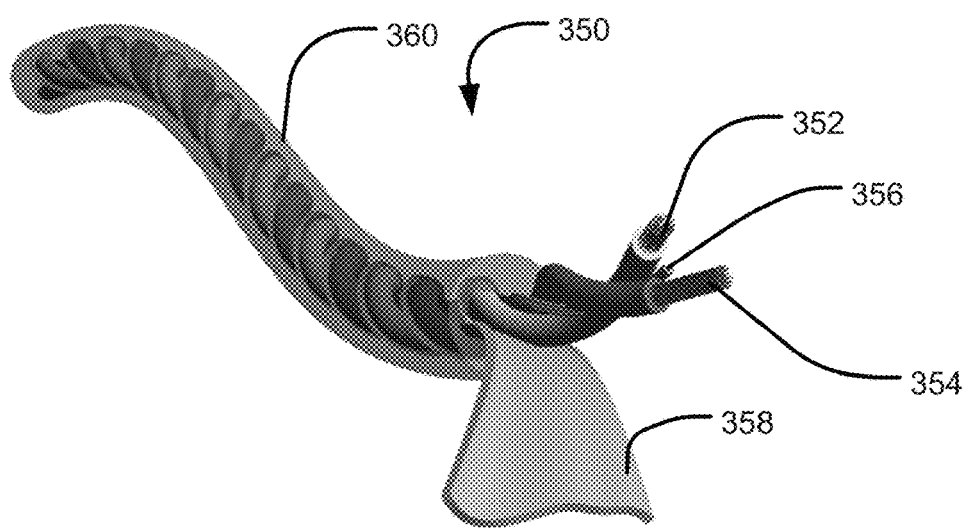
FIG. 3D is a perspective view of the power feed cable in FIG. 3C according to an embodiment.

FIG. 3C is a cross-sectional view of a power feed cable 350 according to some embodiments, though not necessarily drawn to scale. FIG. 3D illustrates a perspective view of the power feed cable 350 according to some embodiments. As discussed above with reference to FIGS. 3A and 3B, the power feed cable 350 includes a first insulated conductor 352 and a second insulated conductor 354. In addition, in this embodiment the power feed includes an uninsulated or bare ground conductor 356. According to some embodiments, the first and second insulated conductors include a center conductor that can be made from any suitable conductive material (e.g., copper or a copper alloy), several examples of which are known in the art. The uninsulated ground conductor 356 can in some cases be made from the same material as the center conductors of the insulated conductors 352, 354, or may be any other suitable conductive material. The insulated covering about the center conductor of insulated conductors 352, 354 can be made from any suitable material having sufficient insulative properties, such as a polymeric material.

Although not shown in FIG. 3C, in some cases the first and second insulated conductors and the bare ground conductor are twisted together along at least part, or optionally the entire length of the power feed cable 350. As mentioned above, providing the power feed cable 350 with such a twisted configuration can in some cases assist in reducing or eliminating certain low-frequency electromagnetic radiation emanating from the power feed 350. For example, as is known, currents traveling in opposing directions through the first and second insulated conductors 352, 354 will generate magnetic fields of opposite polarity that tend to cancel each other or reduce the overall magnetic field presence.

In some embodiments a power feed cable includes a metallic shielding 358 surrounding the first and the second insulated conductors 352, 354. The shielding 358 also surrounds and additionally makes electrical contact with the uninsulated ground conductor 356. The metallic shielding 358 can be formed form any suitable metallic material that has a tendency to reduce the transmission of electric fields. In some cases, the metallic shielding 358 may be a solid, metallic foil wrapped about the conductors 352, 354, 356. For example, during manufacture, the foil may be wrapped about the conductors as they are twisted together. In addition, in some cases the bare ground conductor 356 serves to electrically couple a "true earth ground" to the metallic shielding wrap 358.

FIG. 3C also illustrates an outer protective, insulating jacket 360 surrounding the shielding 358. The jacket 360 can be made from any usual material suitable for protecting and insulating conductors, such as polymeric and/or rubber coatings.

Because of its construction, it will be appreciated that the metallic shielding 358 of the power feed cable 316 can be useful for inhibiting the transmission of low-frequency electric fields that are part of the electromagnetic radiation generated by currents passing through the insulated conductors as forced by the system voltage imposed on the conductors. Accordingly, this embodiment provides a twisted configuration of the insulated conductors 352, 354 in combination with the metallic shielding 358 and bare ground conductor 356 to help further reduce electromagnetic field emissions from the power feed cable 350. As just one example, this can be beneficial when multiple lengths of power cable must be routed through the walls of a sauna in order to electrically couple heating panels to one or more common power sources.

Figure 4A:
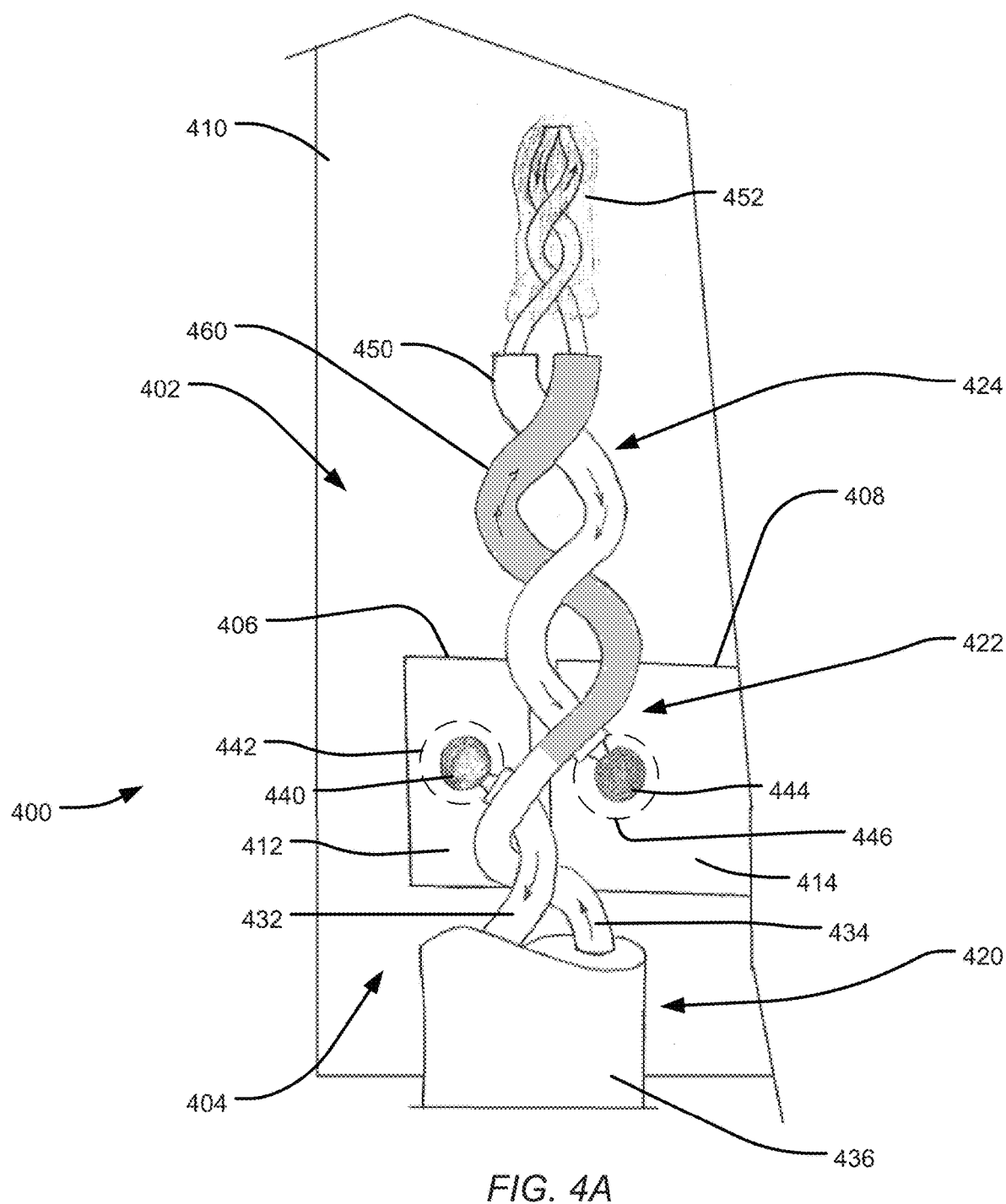
FIG. 4A is a schematic top view of a power connection portion of a sauna heating panel according to an embodiment.

FIG. 4A is a schematic top view of part of a sauna heating panel 400 illustrating a power connection portion 402 of the heating panel according to some embodiments. In this embodiment, a power feed 404 is electrically connected to portions of two power bus bars 406, 408 providing power to one or more heating elements (not shown) in a manner similar to the examples shown in FIGS. 3A and 3B. For example, the power bus bars 406, 408 may provide power to one or more resistive heating elements and/or one or more infrared radiant heating elements.

As shown in FIG. 4A, the first bus bar 406 is positioned below the second bus bar 408, which is attached to the top surface of the heating panel substrate 410. The bottom bus bar 406 may be attached to the bottom surface of the substrate 410 or otherwise positioned within the substrate. In this example, an end portion of the first bus bar 406 provides a first electrical terminal 412 for electrically coupling part of the power feed 404. An end portion of the other bus bar 408 provides a second electrical terminal 414 for electrically coupling another part of the power feed 404. In this case the first and second terminals are configured as strips or pads of conductive material, though it should be appreciated that this is just one possible embodiment.

As shown in FIG. 4A, the power feed 404 can be described as having three separate portions: a supply portion 420, a connection portion 422, and an extension portion 424. In general, the supply portion 420 in this embodiment is provided at least in part by an electrical power cable 430, which in some cases may be similar to the power feed cable 350 described in FIG. 3C. The power cable 430 generally provides an electrical connection between the heating panel 400 and a power source, such as a wall outlet and/or an intermediate power hookup like a power junction/distribution box that may supply power to multiple heating panels. In this example, the power cable 430 and more generally, the supply portion 420, includes first and second insulated conductors 432, 434 having a twisted configuration within an outer protective jacket 436. The power cable 430 may have other elements that are not illustrated in this simplified schematic drawing, including but not limited to one or more parts of the power feed cable 350 shown in FIG. 3C.

For the embodiment illustrated in FIG. 4A, the connection portion 422 of the power feed 404 includes a first electrical coupling or connection between the first insulated conductor 432 and the first terminal 412, which in this case is provided by a solder connection 440 at a first connection point on the first terminal 412 illustrated with a dashed circle 442. The connection portion 422 also includes a second electrical coupling between the second insulated conductor 434 and the second terminal 414, which in this case is provided by an electrical conduction path through the extension portion 424 of the power feed 404 and ending at a solder connection 444 to the second terminal 414 at a second connection point illustrated with another dashed circle 446. As shown in FIG. 4A, in this embodiment, the first and the second terminals 412, 414 are positioned adjacent to one another on the substrate 410, though this may not always be necessary in all embodiments. In addition, other forms of terminals may be used and/or additional electrical components may be provided as part of the electrical couplings depending upon the desired electrical characteristics for a particular design.

According to some embodiments, the extension portion 424 of the power feed generally includes one or more insulated conductors that are in a twisted configuration extending away from the first and second terminals 412, 414 such that current entering and/or leaving the heating panel 400 through the power feed 404 flows in opposite directions through the extension portion in order to reduce electromagnetic field emissions generated by current as is moves flows through the power feed. In the particular embodiment illustrated in FIG. 4A, the extension portion 424 is provided by an extension of the second insulated conductor 434 twisted about a separate return conductor 450. The separate return conductor 450 is provided as a piece of insulated conductor that is initially separate from the second insulated conductor 434, but that is then physically and electrically connected to the end of the second insulated conductor extension at a solder joint 452. The return conductor 450 then returns back to the second terminal 414, where it is also connected to the second connection point 446 by the solder connection 444. The return conductor 450 thus provides an indirect electrical coupling between the power feed 404 (specifically the second insulated conductor 434) and the second terminal 414.

As will be appreciated, the one or more insulated conductors of the extension portion 424 can be provided in many different configurations, using various connections of one or more physically separate but electrically connected conductors to provide the depicted current path having a twisted configuration. As one example, an extension conductor or extension conductor portion 460 (conceptually indicated as the shaded portion of the second insulated conductor in FIG. 4A) extending away from the second terminal 414 may initially be physically separate from, but then electrically connected to, the second conductor 434 to form part of the extension portion 424. In other cases, the extension conductor 460 may be an integral portion of the second insulated conductor 434 as shown in the embodiment of FIG. 4A. Similarly, the return conductor 450 may be a physically separate conductor portion connected to the extension portion 460 as illustrated in FIG. 4A, or may be formed for an integral portion of another conductor also forming the extension conductor 460 and/or the second conductor 434. As will be discussed in further detail later herein, in some cases, the return conductor 450 may initially be a portion of the first insulated conductor 432 that is twisted about and soldered to the end of the second insulated conductor 434, and then subsequently separated from the portion of the first insulated conductor 432 that is part of the power feed supply portion 420.

As previously mentioned, as current enters the heating panel 400 through one insulated conductor and leaves through the other insulated conductor the configuration of the power feed 404 including the extension portion 424 provides additional capabilities for reducing low-frequency electromagnetic field emissions generated by the current as is moves flows through the power feed. As will be appreciated, in a typical state of the art power feed connection, insulated conductors may be simply directly connected to respective terminals (i.e., without the use of the extension portion 424 shown in FIG. 4A). In some cases there may be some field cancelling effect caused by twisting of the conductors as they approach the terminals. However, in many cases, at least a portion of one of the conductors may not have a corresponding twisted conductor, and so some uncancelled fields can radiate from the heating panel. It is believed that configurations such as the twisted configuration of the extension portion 424 of the power feed in FIG. 4A provide additional field cancelling effects that can reduce electromagnetic fields generated by such types of power feeds even further.

Figure 4B:
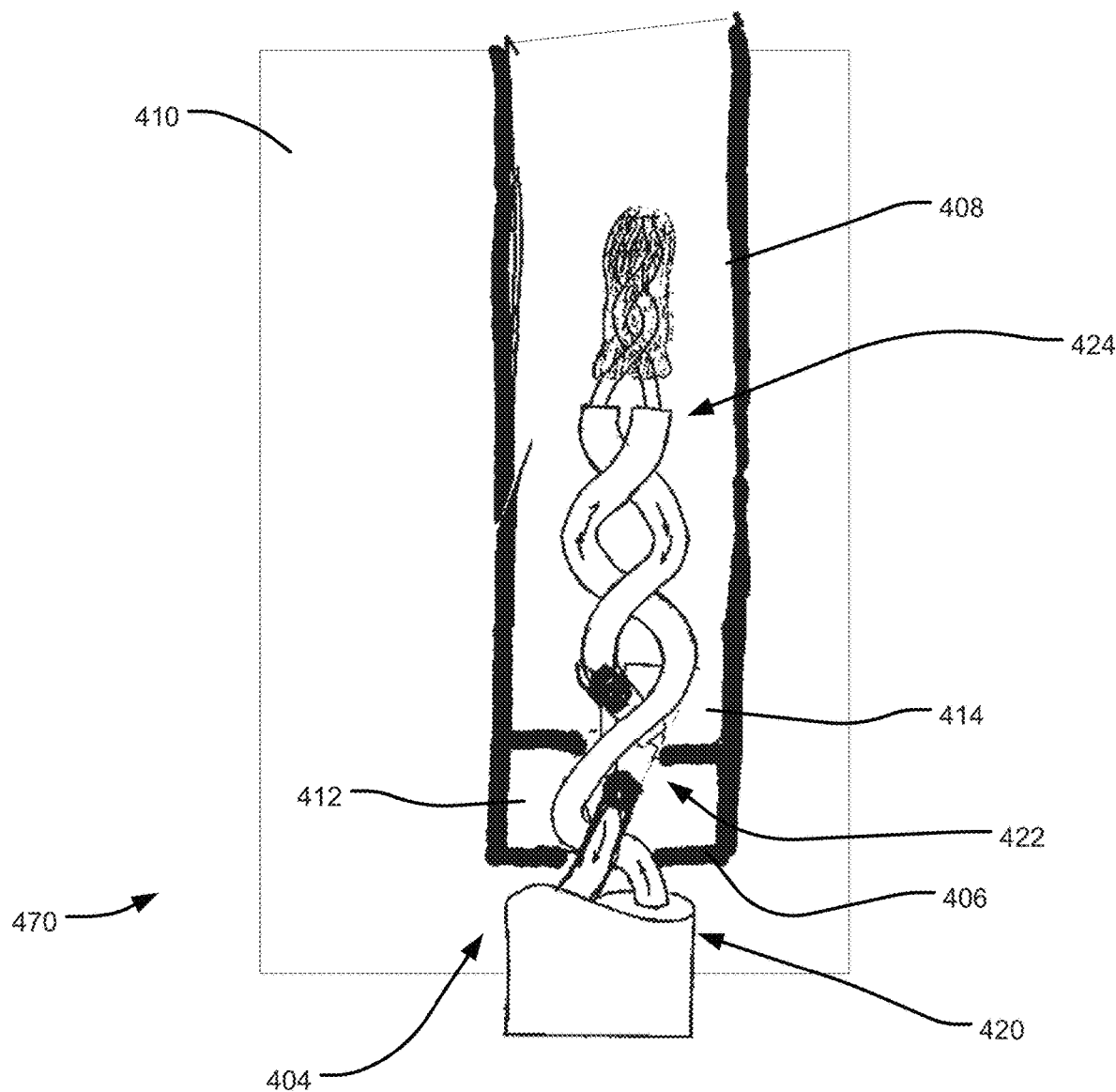
FIG. 4B is a schematic top view of another power connection portion of a sauna heating panel according to an embodiment.

In the embodiment shown in FIG. 4A, the power feed 404 is positioned on the substrate 410 and connected to the terminals 412, 414 such that the power feed 404 is generally perpendicular to the first and second power bus bars 406, 408. Of course other orientations, including parallel and/or angles less than or greater than 90 degrees to the bus bars 406, 408 are also possible for embodiments including power bus bars or in any other desirable embodiment. FIG. 4B illustrates one possible embodiment of a heating panel 470 in which the power feed 404 is positioned on the heating panel substrate 410 so that it has a generally parallel orientation with the first and second power bus bars 406, 408. In some cases, a parallel orientation and/or other orientations can be provided by changing the exact location of the electrical connection points for the power feed 404 on the first and second terminals and/or bending the extension portion 424 in various directions.

Figure 5:
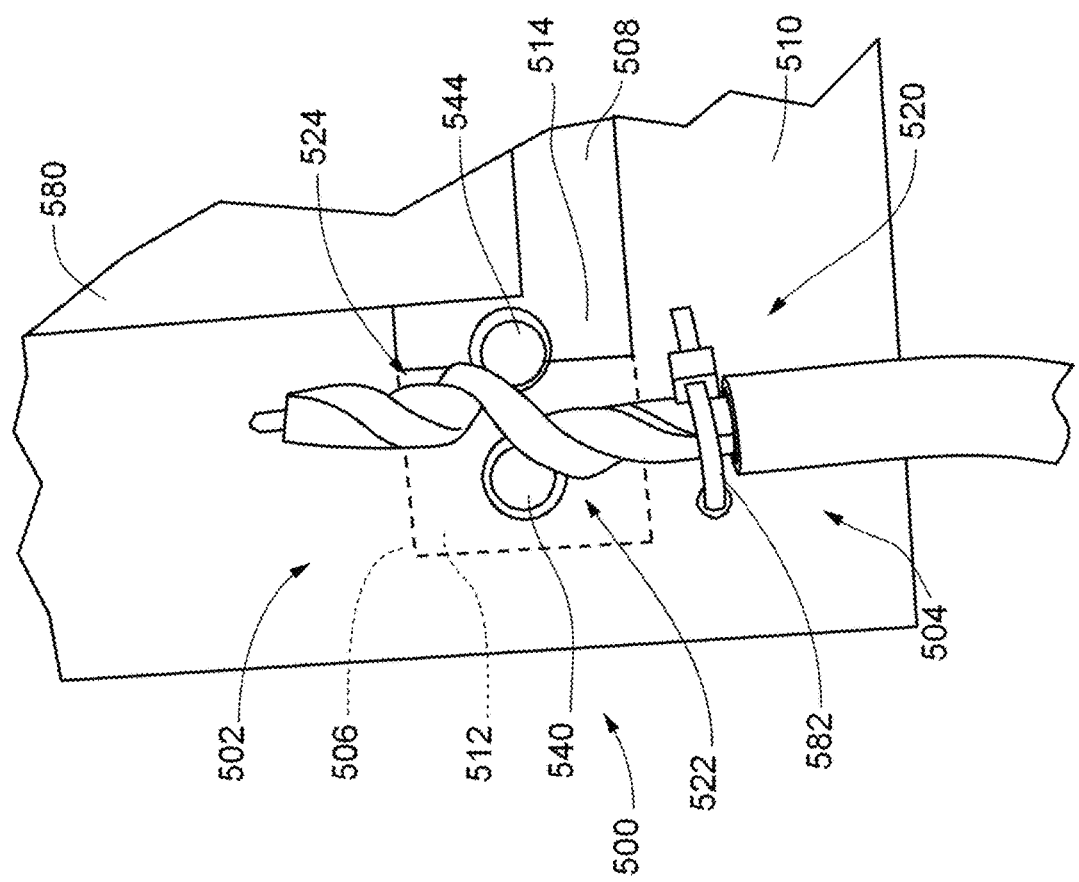
FIG. 5 is a top view of a power connection portion of an infrared heating panel according to an embodiment.
Figure 7A:
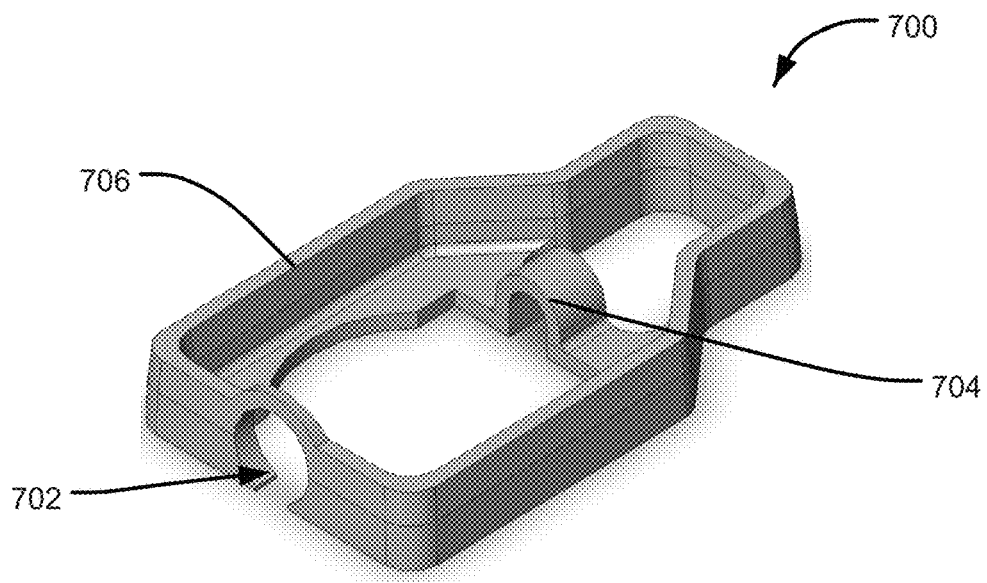
FIGS. 7A-7D are views of a containment shell for a heating panel power feed according to an embodiment.
Figure 7B:
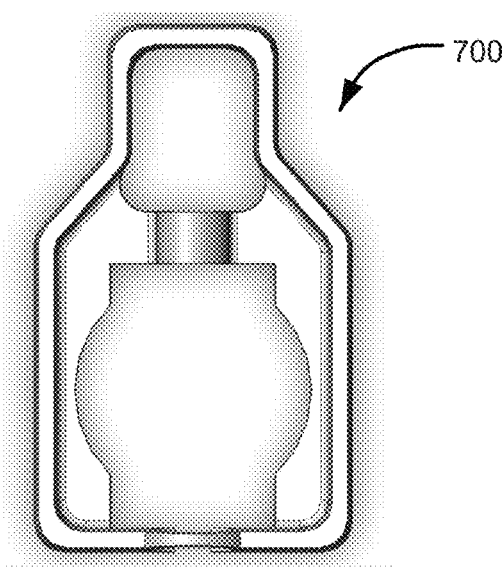
Figure 7C:
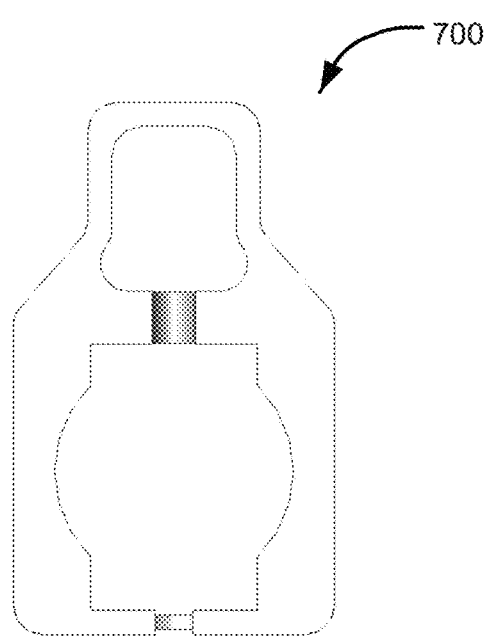
Figure 7D:
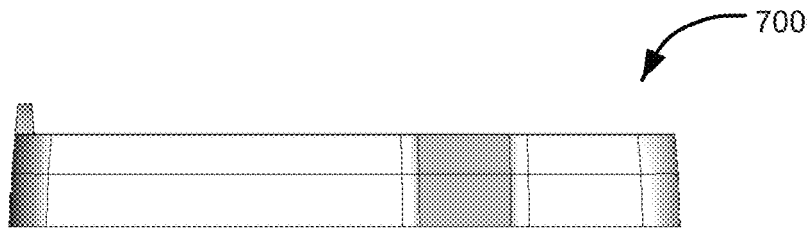
Figures 8A, 8B, 8C, 8D:
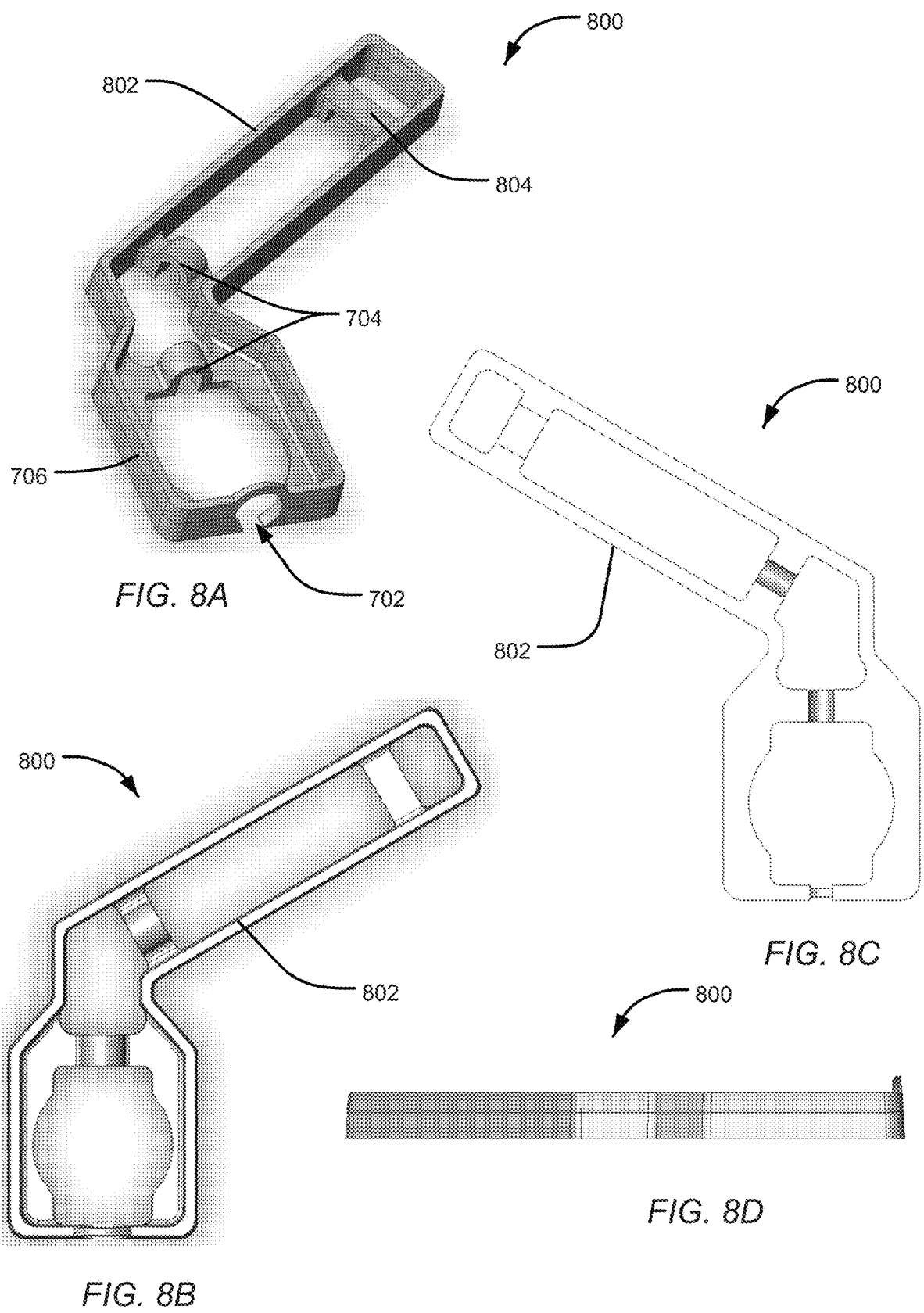
FIGS. 8A-8D are views of a containment shell for a heating panel power feed including a thermal switch according to an embodiment.

FIG. 5 is a top view of part of a sauna heating panel 500 illustrating a power connection portion 502 of the heating panel according to some embodiments. In viewing FIG. 5, it will be appreciated that the heating panel 500 includes a number of features similar to the heating panel 400 shown in FIG. 4A. In this embodiment, the heating panel 500 includes a substrate 510 that is made from an insulative fiberglass material used to make printed circuit boards. One power bus bar 508 extends across one surface of the substrate 510 and ends in a terminal 514 similar to the embodiment in FIG. 4A. Another power bus bar 506 is positioned below the top bus bar 508 and ends in a terminal 512. A power feed 504 is electrically coupled to the first and second terminals 512, 514, for providing power to one or more heating elements 580 connected to the bus bars 506, 508 in a manner similar to the examples shown in FIGS. 3A and 3B. In this example, the power bus bars 506, 508 may provide power to a plurality of infrared radiant heating elements 580. Examples of some types of possible infrared heating elements are described in U.S. patent application Ser. No. 12/966,221.

As shown in FIG. 5, in this case the power feed 504 is secured to the substrate 510 with a fastener 582 in addition to being secured by solder connections 540, 544 electrically and physically connecting a connection portion 522 of the power feed 504 to the first and second terminals, respectively. In this embodiment, the power feed 504 also includes an extension portion 524 that extends across the substrate (as well as across one or more of the terminals), past the solder connections 540, 544 and their respective electrical connection points on the substrate 510, and past the edge of the terminals 512, 514, in a perpendicular orientation with respect to the bus bars 506, 508. According to some embodiments, the extension portion 524 of the power feed 504 may extend past the terminals for any of a variety of lengths. According to some embodiments, the extension portion 524 extends at least 2 centimeters and in some cases up to 2.5 or more centimeters. Of course embodiments are not limited to any particular length for an extension portion 524 of a power feed 504.

Figure 6:
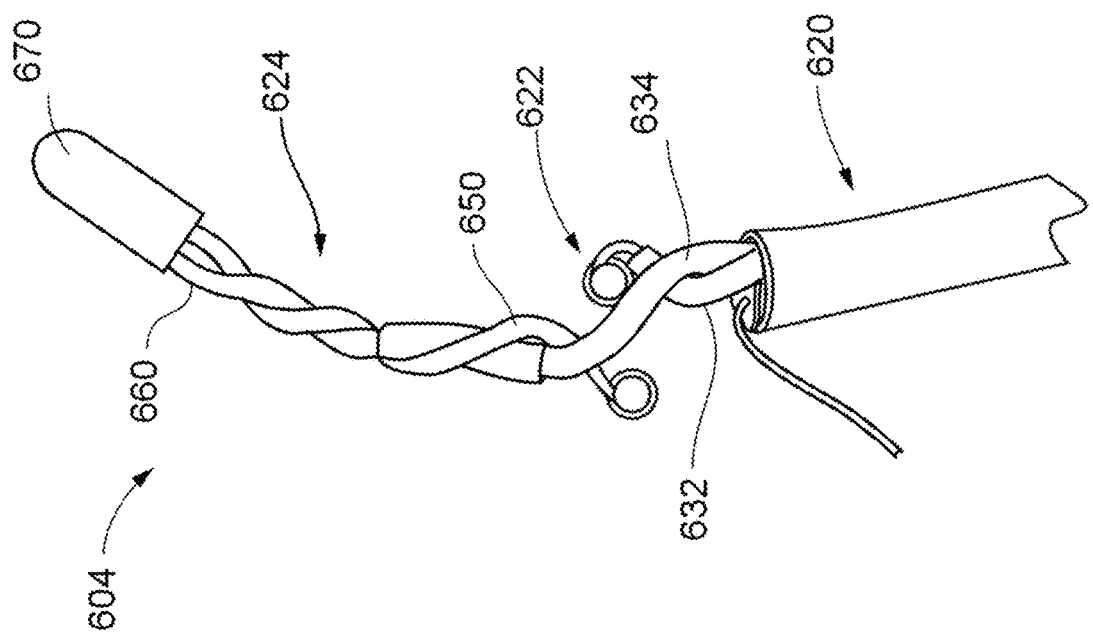
FIG. 6 is a top view of a power connection portion of an infrared heating panel including a thermal switch according to an embodiment.

FIG. 6 is a top view of a power feed 604 including a thermal switch 670 according to some embodiments. The power feed 604 is similar in many respects to the power feeds described above, but in this case includes the thermal switch 670, which can be useful for sensing the temperature of a heating element and in some cases disconnecting the power feed 604 from one or more heating elements based on the temperature sensing by the thermal switch 670. According to some embodiments, the term thermal switch may also be considered to mean a thermal breaker or thermal circuit breaker.

As shown in FIG. 6 apart from a heating panel, in this embodiment, the power feed 604 includes a supply portion 620 having first and second insulated conductors 632, 634, a connection portion 622 configured to connect the power feed to respective terminals on the heating panel, and an extension portion 624 which in this case includes the thermal switch 670. In some cases, the thermal switch 670 may be provided with first and second integrated leads in a twisted configuration, which can be used as at least part of an extension conductor 660 and as at least part of a return conductor 650 of the power feed extension portion 624. The switch lead making up the extension portion 624 in this case is electrically and physically connected to an end of the power feed's second insulated conductor 634. The switch lead making up the return conductor portion 650 is configured to be physically and electrically connected to a terminal of a heating panel, for example by a solder connection. Accordingly, the extension and return conductors (switch leads in this case) are configured along with the thermal switch 670 to provide an indirect electrical coupling between the second insulated conductor and a terminal of the heating panel.

Figure 10:
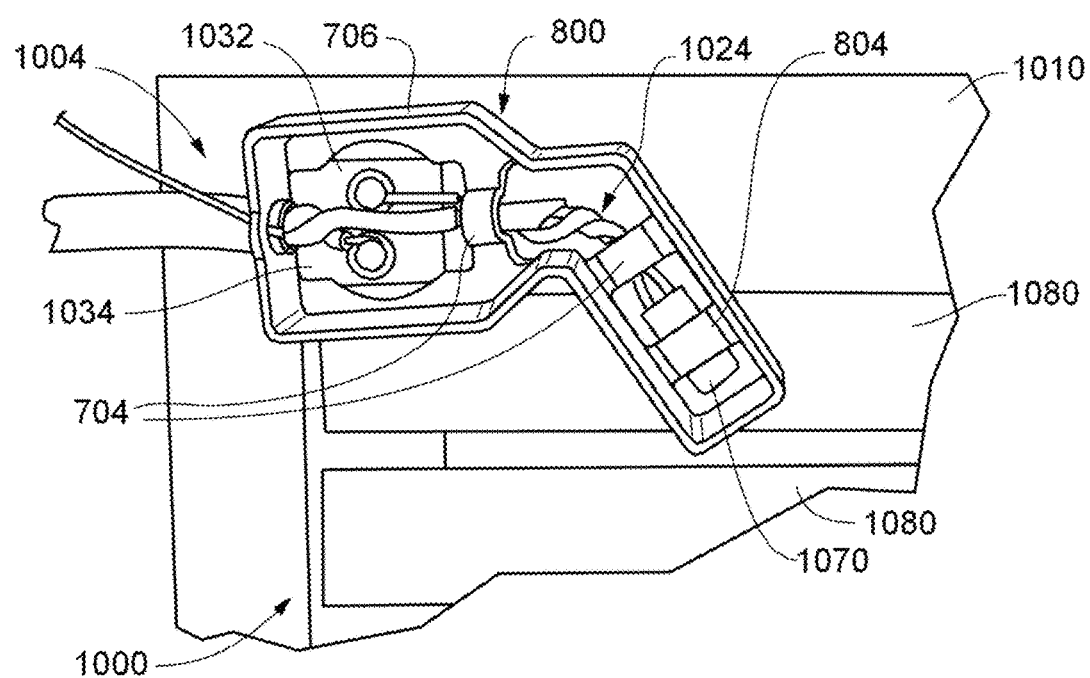
FIG. 10 is a top view of a power connection portion of an infrared heating panel including a thermal switch according to an embodiment.

Referring briefly to FIG. 10, an example of a power feed 1004 similar to the power feed 604 is shown positioned on the substrate 1010 of a heating panel 1000 according to some embodiments. According to some embodiments, the power feed 1004 is secured to the heating panel substrate 1010 with a containment shell 800, as will be further discussed hereinafter. The extension portion 1024 of the power feed 1004 extends over the substrate 1010, in this case between the first and second terminals 1032, 1034 and one of the heating elements 1080 positioned on the heating panel substrate. The extension portion 1024 also includes a thermal switch 1070 located at the end of the extension portion that is positioned on the heating element 1080 nearest the power feed 1004. As shown in FIG. 10, the extension portion 1024 is angled toward the heating element 1080 to position the thermal switch on the heating element 1080. Of course, it should be appreciated that the extension portion 1024 and the thermal switch 1070 could approach the heating element 1080 from any number of angles, including directly perpendicular to the heating element. The angle of approach can depend upon factors, such as, for example, the location and orientation of the first and second terminals 1032, 1034, the size and shape of the substrate 1010, and the location and orientation of the power feed 1004, to name just a few.

Turning to FIGS. 7A-7D and 8A-8D, examples of possible containment systems for containing one or more portions of a power feed and securing the power feed to the substrate of a heating panel will now be described. Referring to FIGS. 7A-7D, several views are depicted of a containment shell 700 that can be useful as part of a containment system for a heating panel power feed according to some embodiments. The containment shell 700 is generally configured as an insulative form or frame configured to contain at least part of a heating panel power feed. In the example shown in FIGS. 7A-7D, the containment shell 700 is generally configured to receive the connection portion 522, the extension portion 524, and at least part of the supply portion 520 of the power feed 504 and their respective insulative conductors shown in FIG. 5. In this case, for example, the containment shell 700 includes a supply portion opening 702 and an extension portion clamp 704 configured to receive and hold the respective portions of the power feed within the shell 700.

The shell 700 further includes an exterior wall 706 as shown in FIGS. 7A-7D. According to some embodiments, an insulative adhesive, such as an epoxy, is poured into the interior of the shell 700 created by the wall 706 to surround and insulate the contained portions of the power feed while also adhering the power feed and the shell 700 to the heating panel substrate. The containment shell 700 can be made from any suitable insulative material. As just one example, in some cases the containment shell 700 may be a component that is injection-molded from one or more polymers.

Figure 9:
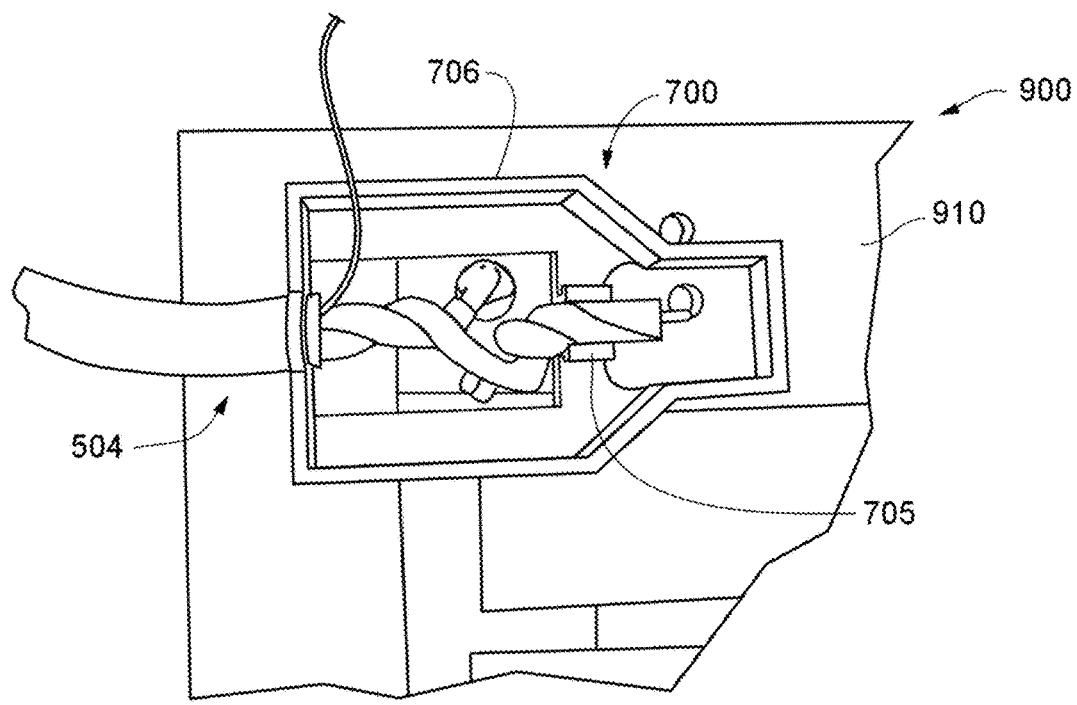
FIG. 9 is a top view of a power connection portion of an infrared heating panel according to an embodiment.

FIG. 9 provides a top view of a modified version of the shell 700 (with another version of an extension portion clamp 705) being used in a containment system on a heating panel 900. As is shown, the shell 700 surrounds and contains portions of the power feed 504 from FIG. 5 upon the substrate 910 of the heating panel 900. Although omitted from FIG. 9 for clarity, an insulative adhesive can be used to fill the interior of the containment shell 700, surround the contained portions of the power feed 504, and attach both the power feed 504 and the containment shell 700 to the substrate 911.

Returning to FIGS. 8A-8D, several views are provided of another containment shell 800 previously discussed with respect to FIG. 10. The containment shell 800 includes many of the same features described above with respect to the containment shell 700 shown in FIGS. 7A-7D, several of which are shown in FIGS. 8A-8D with identical reference numbers. In this embodiment the containment shell 800 also includes an elongated and angled extension portion 802 configured to contain the longer extension portion 624 and thermal switch 670 of the power feed 604 shown in FIG. 6. In addition, the shell 800 also includes an additional extension portion clamp 704 for better securing the longer extension portion and also includes a thermal switch clamp 804 configured to secure the thermal switch 670 prior to introducing an insulative adhesive into the shell 800. Returning to FIG. 10, the containment shell 800 is positioned about the power feed 1004 on the heating panel substrate 1010 as previously discussed. In some cases, though not necessarily all, an insulative adhesive such as an epoxy is used to fill the interior of the containment shell 800, surround the contained portions of the power feed 1004, and attach both the power feed 1004 and the containment shell 800 to the substrate 1010.

According to some embodiments, methods are also provided for powering a heating panel of a sauna and/or providing a power connection to a sauna heating panel, such as an infrared heating panel as discussed above with respect to some examples. According to one embodiment, a method for providing a power connection to a heating panel of a sauna is provided. The method includes providing a heating panel and a power feed, such as one of the heating panels and/or power feeds described herein. For example, the heating panel can include a substrate, at least one heating element, and first and second terminals electrically coupled to the at least one heating element. The power feed can include a first insulated conductor, a second insulated conductor in a twisted configuration with the first insulated conductor, an extension conductor portion electrically connected to the second insulated conductor, and a return conductor portion electrically coupled to the extension conductor portion. The return conductor portion is twisted about the extension conductor portion. The method further includes electrically connecting the first insulated conductor to the first terminal and extending the extension conductor portion across the substrate past the second terminal. The method also includes returning the return conductor portion across the substrate to the second terminal and electrically connecting the return conductor portion to the second terminal.

According to some embodiments, the extension conductor portion of the power feed is a portion of the second insulated conductor and the return conductor portion is a portion of the first insulated conductor in a twisted configuration with the portion of the second insulated conductor. In such cases, methods can further include electrically connecting an end of the portion of the second insulated conductor with an end of the portion of the first insulated conductor and then extending the portions of the first and the second insulated conductors across the substrate past the first and the second terminals. Such methods can also include cutting the first insulated conductor to separate the return conductor portion from a supply portion of the first insulated conductor. The methods may further include electrically connecting the first insulated conductor to the first terminal and electrically connecting the return conductor portion to the second terminal. In some embodiments, one or more methods may also include electrically coupling a thermal switch to the power feed. For example, if a thermal switch includes its own integral leads, the switch leads can optionally act as part or all of the extension conductor portion and/or return conductor portion Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A method for providing a power connection to a heating panel of a sauna, comprising:
    providing the heating panel for the sauna, the heating panel comprising a substrate, at least one heating element, and first and second terminals electrically coupled to the at least one heating element;
    providing a power feed comprising a first insulated conductor, a second insulated conductor in a twisted configuration with the first insulated conductor, an extension conductor portion electrically connected to the second insulated conductor, and a return conductor portion electrically coupled to the extension conductor portion;
    electrically connecting the first insulated conductor to the first terminal;
    extending the extension conductor portion across the substrate past the second terminal;
    returning the return conductor portion across the substrate to the second terminal, the return conductor portion in a twisted configuration with the extension conductor portion; and
    electrically connecting the return conductor portion to the second terminal.

2. The method of claim 1, wherein the extension conductor portion is an integral first portion of the second insulated conductor and the return conductor portion is an integral second portion of the second insulated conductor integrally connected to an end of the integral first portion of the second insulated conductor.

3. The method of claim 1, wherein the extension conductor portion is a portion of the second insulated conductor and the return conductor portion is a portion of the first insulated conductor in a twisted configuration with the portion of the second insulated conductor, and further comprising
  electrically connecting an end of the portion of the second insulated conductor with an end of the portion of the first insulated conductor,
  extending the portions of the first and the second insulated conductors across the substrate past the first and the second terminals,
  cutting the first insulated conductor to separate the return conductor portion, and then
  electrically connecting the first insulated conductor to the first terminal and electrically connecting the return conductor portion to the second terminal.

4. The method of claim 1, wherein the power feed further comprises a thermal switch, a first switch lead providing at least part of the extension conductor portion, and a second switch lead providing at least part of the return conductor portion.

5. A method for providing a power connection to a heating panel of a sauna, comprising:
  providing the sauna heating panel, the sauna heating panel comprising a substrate, at least one heating element, and first and second terminals electrically coupled to the at least one heating element;
  providing a power feed, the power feed comprising a first conductor, a second conductor, an uninsulated ground conductor, a metallic shielding, and an insulating jacket; and
  electrically coupling the power feed to the first and second terminals of the sauna heating panel;
  wherein the first conductor, the second conductor, and the uninsulated ground conductor have a twisted configuration;
  wherein the metallic shielding surrounds the twisted configuration of the first conductor, the second conductor and the uninsulated ground conductor;
  wherein the insulating jacket surrounds the metallic shielding; and
  wherein the metallic shielding is in electrical contact with the uninsulated ground conductor, for coupling the metallic shielding to ground.

6. The method of claim 5, wherein the power feed further comprises an extension conductor portion and a return conductor portion electrically coupled to the extension conductor portion;
  wherein the extension conductor portion and the return conductor portion have a twisted configuration; and
  further comprising extending the extension conductor portion and the return conductor portion across the substrate and away from the first and the second terminals.

7. The method of claim 5, wherein the metallic shielding is in electrical contact with the uninsulated ground conductor along a length of the power feed.

8. The method of claim 5, further comprising electrically coupling the uninsulated ground conductor to an earth ground, thereby coupling the metallic shielding to the earth ground.

9. A method for providing a power connection to a heating panel of a sauna, comprising:
  providing the sauna heating panel, the sauna heating panel comprising a substrate, at least one heating element, and first and second terminals electrically coupled to the at least one heating element;
  providing a power feed, the power feed comprising a first conductor, a second conductor, an extension conductor portion, and a return conductor portion, the extension conductor portion and the return conductor portion having a twisted configuration;
  electrically connecting the first conductor to the first terminal;
  electrically connecting the return conductor portion to the second terminal;
  extending the extension conductor portion and the return conductor portion across the substrate and away from the first and the second terminals; and
  containing the first terminal, the second terminal, the extension conductor portion, and the return conductor portion on the substrate with a containment system.

10. The method of claim 9, wherein containing the first terminal, the second terminal, the extension conductor portion, and the return conductor portion on the substrate comprises positioning a containment shell about the first terminal, the second terminal, the extension conductor portion, and the return conductor portion.

11. The method of claim 10, further comprising attaching the containment shell to the substrate, thereby securing the extension conductor portion and the return conductor portion upon the substrate.

12. The method of claim 11, wherein attaching the containment shell to the substrate comprises filling the containment shell with an insulative adhesive.

13. The method of claim 9, wherein the containment system comprises a clamp and wherein containing the extension conductor portion and the return conductor portion on the substrate comprises holding the twisted configuration of the extension conductor portion and the return conductor portion with the clamp.

14. The method of claim 9, wherein the power feed comprises a thermal switch electrically coupled to the extension conductor portion and the return conductor portion, wherein the containment system comprises a containment shell comprising a first shell portion positioned about the first terminal and the second terminal and a second shell portion positioned about the thermal switch, at least part of the extension conductor portion, and at least part of the return conductor portion, and wherein the second shell portion extends across the substrate from the first shell portion toward the at least one heating element.

15. An infrared heating panel for a sauna, comprising:
  a substrate;
  at least one infrared heating element supported by the substrate and configured to provide heat for a user of the sauna;
  first and second terminals electrically coupled to the at least one infrared heating element;
  a first conductor for providing power to the at least one infrared heating element, the first conductor comprising a first end electrically connected to the first terminal and a second end for connecting to an electrical power source;
  a second conductor for providing power to the at least one infrared heating element, the second conductor comprising a first end for connecting to the second terminal and a second end for connecting to the electrical power source, wherein the second conductor is twisted about the first conductor;

an extension conductor electrically connected to the first end of the second conductor and extending past the second terminal and across the substrate away from the second terminal; and a return conductor that is electrically coupled to the extension conductor, the return conductor being electrically connected to the second terminal and twisted about the extension conductor.

16. The heating panel of claim 15, wherein the extension conductor is an integral first portion of the second conductor and the return conductor is a separate conductor physically connected to an end of the extension conductor.

17. The heating panel of claim 15, further comprising a thermal switch electrically coupled between the extension conductor and the return conductor.

18. The heating panel of claim 15, further comprising a containment system attached to the substrate and positioned about the first and the second terminals, the extension conductor, the return conductor, at least a portion of the first conductor and at least a portion of the second conductor.

19. The heating panel of claim 18, wherein the containment system comprises a shell configured to hold the extension conductor, the return conductor, the first conductor, and the second conductor against the substrate, and further comprising an insulating adhesive filling the shell and attaching the shell to the substrate.

20. The heating panel of claim 15, wherein the extension conductor is an integral first portion of the second conductor and the return conductor is an integral second portion of the second conductor integrally connected to an end of the integral first portion of the second conductor.

21. The heating panel of claim 15, further comprising:
a first power bus supported by the substrate;
a second power bus supported by the substrate, the first and the second power buses positioned one over the other in an overlapping parallel configuration; and
a plurality of heating elements supported by the substrate, each of the heating elements electrically coupled to the first power bus and the second power bus;
wherein the first terminal is provided by the first power bus; and
wherein the second terminal is provided by the second power bus.

22. The heating panel of claim 21, wherein the extension conductor is substantially perpendicular to the first power bus and the second power bus.

* * * * *